United States Patent
Czerw et al.

(10) Patent No.: US 7,302,851 B2
(45) Date of Patent: Dec. 4, 2007

(54) METHODS AND APPARATUS FOR ROTARY MACHINERY INSPECTION

(75) Inventors: Gerald John Czerw, Scotia, NY (US); Laurie Diane Donovan, Cat Spring, TX (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/617,198

(22) Filed: Dec. 28, 2006

(65) Prior Publication Data

US 2007/0119255 A1 May 31, 2007

Related U.S. Application Data

(62) Division of application No. 10/736,363, filed on Dec. 15, 2003, now Pat. No. 7,174,788.

(51) Int. Cl.
*G01N 29/04* (2006.01)

(52) U.S. Cl. ...................................................... 73/620

(58) Field of Classification Search ................. 73/620, 73/621, 625, 626, 627, 628, 629
See application file for complete search history.

(56) References Cited

U.S. PATENT DOCUMENTS

| | | | |
|---|---|---|---|
| 3,678,736 A * | 7/1972 | May ............................ | 73/634 |
| 4,194,400 A * | 3/1980 | Staff ........................... | 73/623 |
| 5,408,884 A | 4/1995 | Sabourin | |
| 5,421,200 A | 6/1995 | Casarcia et al. | |
| 5,515,728 A | 5/1996 | Casarcia et al. | |
| 5,980,209 A | 11/1999 | Barry et al. | |
| 6,065,344 A | 5/2000 | Nolan et al. | |
| 6,082,198 A | 7/2000 | Sabourin et al. | |
| 6,416,284 B1 | 7/2002 | Demers et al. | |
| 7,017,414 B2 | 3/2006 | Falsetti et al. | |
| 7,093,491 B2 | 8/2006 | Murphy et al. | |

OTHER PUBLICATIONS

J. Krautkramer et al., Ultrasonic Testing of Material, 3rd Edition, Springer-Verlag, New York, 1983, Section 20.2, "Worked Parts of Machines," pp. 371-380.*

* cited by examiner

*Primary Examiner*—John E. Chapman
(74) *Attorney, Agent, or Firm*—Armstrong Teasdale LLP

(57) ABSTRACT

A method of non-destructive evaluation (NDE) testing a component of an assembly is provided. The method includes positioning a transducer on a face of the component, transmitting ultrasonic waves into the component at a plurality of steering angles, receiving ultrasonic echoes, wherein each received echo is indicative of an acoustic impedance interface within the component, and analyzing the ultrasonic echoes.

19 Claims, 8 Drawing Sheets

METHODS AND APPARATUS FOR ROTARY MACHINERY INSPECTION

CROSS-REFERENCE TO RELATED APPLICATIONS

This application is a divisional of U.S. patent application Ser. No. 10/736,363, filed Dec. 15, 2003 now U.S. Pat. No. 7,174,788, which is hereby incorporated by reference and is assigned to assignee of the present invention.

BACKGROUND OF THE INVENTION

This application relates generally to gas turbine engines and, more particularly, to methods and apparatus for testing gas turbine engine compressor and turbine rotor assemblies.

At least some known gas turbine engines include a compressor for compressing air, which is mixed with a fuel and channeled to a combustor wherein the mixture is ignited within a combustion chamber for generating hot combustion gases. The hot combustion gases are channeled downstream to a turbine, which extracts energy from the combustion gases for powering the compressor, as well as producing useful work to propel an aircraft in flight or to power a load, such as an electrical generator.

Known compressors include a rotor assembly that includes at least one row of circumferentially spaced rotor blades. Each rotor blade includes an airfoil that includes a pressure side and a suction side connected together at leading and trailing edges. Each airfoil extends radially outward from a rotor blade platform. Each rotor blade also includes an attachment portion, such as, a dovetail that extends radially inward from the platform, and is used to mount the rotor blade within the rotor assembly to a rotor disk or spool. More specifically, at least some known rotor disks include a plurality of circumferentially spaced axially oriented dovetail slots that are sized to receive a respective one of the plurality of rotor blades therein. Known rotor blade dovetails are generally shaped complementary to the disk dovetail slot to enable the rotor blade dovetails and the rotor disk slot to mate together and form a dovetail assembly.

During operation, the rotor blade dovetails may be subjected to loading forces that may cause in-service cracking of the blade dovetails. Known inspection techniques are limited in their ability to assess the integrity of the blade dovetails while the blades are in-place. More specifically, a visual inspection only permits a limited examination of the blades for cracks in the airfoil and in a very limited area of the dovetail. To thoroughly examine the dovetail region, where cracking may also originate, at least a portion of the engine casing may need to be removed to facilitate removal of each blade, and subsequent inspection of the dovetails with visual, magnetic particle, or liquid penetrant techniques. However, because of labor and cost constraints such techniques may be impracticable in some instances.

BRIEF DESCRIPTION OF THE INVENTION

In one aspect, a method of non-destructive evaluation (NDE) testing a component coupled to a rotatable member of a rotary machine while the rotatable member remains coupled within an assembled rotary machine is provided. The method includes positioning a transducer on a face of the component, transmitting ultrasonic waves into the component at a plurality of steering angles, receiving ultrasonic echoes, wherein each received echo is indicative of an acoustic impedance interface within the component, and analyzing the ultrasonic echoes.

In another aspect, an ultrasonic testing system for testing a component of a rotatable member of a rotary machine while the rotatable member remains coupled within an assembled rotary machine is provided. The system includes a transducer configured to transmit ultrasound waves into and receive ultrasound echoes from the component, a transmitter/receiver for transmitting signals to the transducer and for receiving signals indicative of ultrasonic echoes from the transducer, wherein each echo is indicative of an acoustic impedance interface within the component, a processor for controlling outputs from the transmitter/receiver and receiving inputs from the transmitter/receiver, and a display for outputting information based on the ultrasonic echo data.

DETAILED DESCRIPTION OF THE INVENTION

Figure 1:
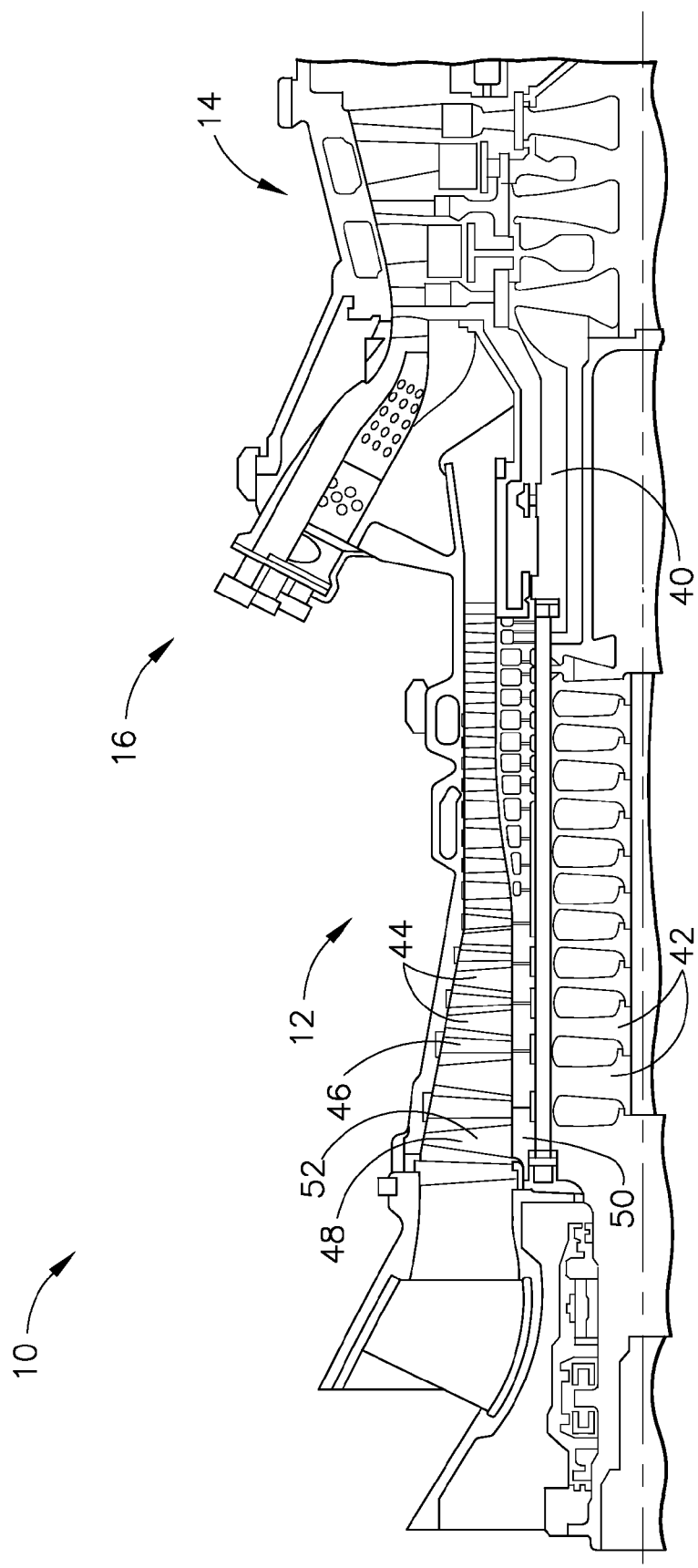
FIG. 1 is a side elevation view of an exemplary gas turbine engine.

FIG. 1 is a side elevation view of an exemplary gas turbine engine 10 that includes a compressor section 12, a turbine section 14 and a plurality of combustors 16 (only one combustor shown in FIG. 1) Engine 10 includes a rotor 40 including a plurality of rotor wheels 42. Each rotor wheel 42 is configured to mount a plurality of components, such as, but not limited to, buckets or blades 44, which in conjunction with a respective number of stator vanes 46, form the various stages of engine 10. In the exemplary embodiment, a plurality of compressor blades 44 are coupled to a first row 48 that includes a first-stage rotor wheel 50. Each blade 44 includes an airfoil 52 that is mounted in opposition to respective first-row stator vanes 54. Blades 44 are spaced circumferentially about first-stage wheel 50. Turbine engine 10 may drive a generator (not shown) for producing electrical power. In the exemplary embodiment, engine 10 is a MS6001B gas turbine engine, commercially available from General Electric Company, Greenville, S.C.

Figure 2:
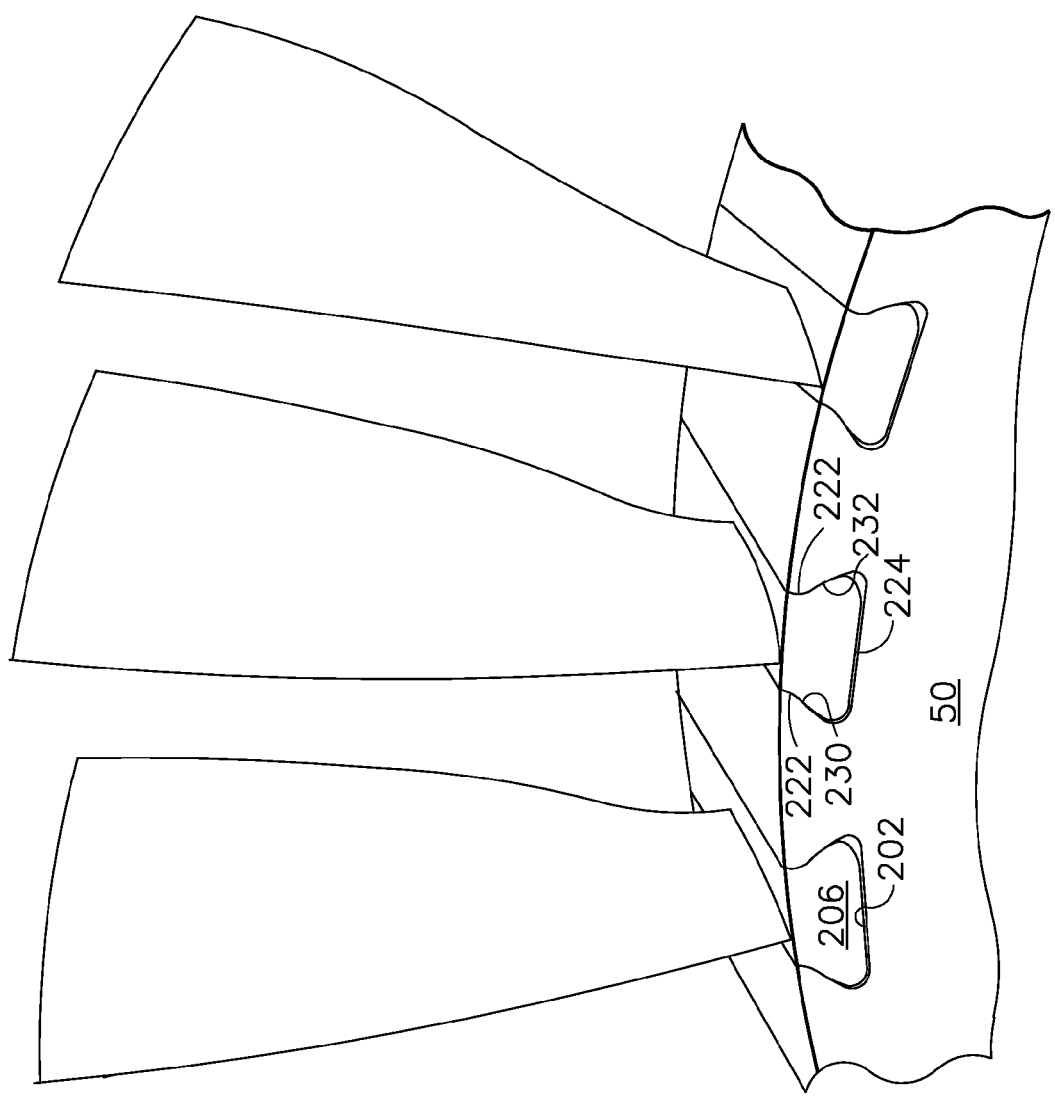
FIG. 2 is a perspective view of a portion of a row one (R1) compressor wheel that may be used with the gas turbine engine shown in FIG. 1.

FIG. 2 is a perspective view of a portion of first stage rotor wheel 50. Rotor wheel 50 includes a plurality of axially aligned dovetail slots 202 that are spaced circumferentially about a radially outer periphery of wheel 50. Slots 202 receive an attachment portion, such as a dovetail 206 of blade 44, therein. More specifically, blades 44 are removably coupled within disk slot 202 by each respective blade dovetail 206. Accordingly, slot 202 is shaped to generally compliment a shape of each dovetail 206 received therein, and accordingly, in the exemplary embodiment, includes a pair of wheel post tangs 222 and a disk slot bottom 224 that extends between wheel post tangs 222. In the exemplary embodiment, disk slot 202 also includes a pair of opposed wheel faces 230 and 232.

Figure 3:
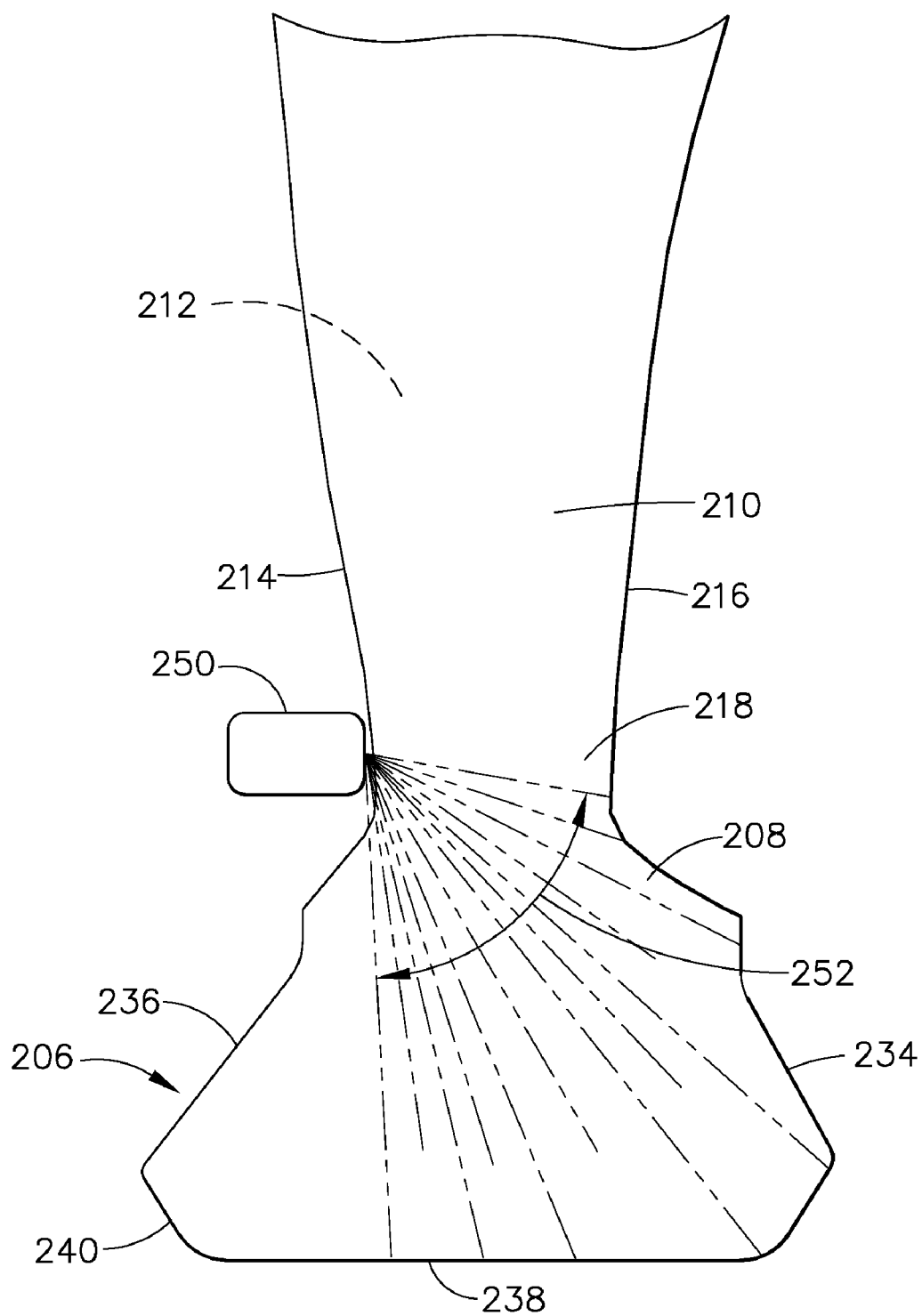
FIG. 3 is an enlarged axial cross-sectional view of a portion of a compressor blade that may used with the compressor wheel shown in FIG. 2.

FIG. 3 is an enlarged axial cross-sectional view of a portion of rotor blade 44. Each rotor blade 44 includes a dovetail 206 used for mounting each respective airfoil 52 to rotor wheel 50. More specifically, each airfoil 52 extends radially outward from a platform 208 formed integrally with, and extending between dovetail 206 and airfoil 52. Each airfoil 52 includes a first contoured sidewall 210 and a second contoured sidewall 212. First sidewall 210 defines a suction side of airfoil 52, and second sidewall 212 defines a pressure side of airfoil 52. Sidewalls 210 and 212 are joined at a leading edge 214 and at an axially spaced trailing edge 216 of airfoil 52. More specifically, airfoil trailing edge 216 is spaced chordwise and downstream from airfoil leading edge 214. First and second sidewalls 210 and 212, respectively, extend longitudinally or radially outward in span from a blade root 218 positioned adjacent dovetail 206, to an airfoil tip 220.

Each blade dovetail 206 is mounted within dovetail slot 202, and cooperates with dovetail slot 202, to form rotor wheel 50. In the exemplary embodiment, each dovetail 206 includes a pair of opposed dovetail shoulders 234 and 236, and a dovetail bottom 238 that extends between dovetail shoulders 234 and 236. A dovetail base 240 extends circumferentially between dovetail shoulders 234 and 236. Shoulders 234 and 236 are sized to be received within respective wheel post tangs 222 and engage disk slot 202, such that blades 44 are radially retained within wheel 50. In an alternative embodiment, each blade dovetail includes a plurality of pairs of wheel post tangs 222.

During operation, centrifugal forces force rotor blades 44 outward and induce loading forces into dovetail 206. Over time, such forces may induce cracking within dovetail 206 at such locations that may be radially inward from platform 208, and thus not easily accessible to conventional testing techniques.

An ultrasonic transducer 250 may be placed in a position contacting blade 44 radially outward from platform 208 to interrogate a volume of dovetail 206 that is inaccessible to known testing techniques. In the exemplary embodiment, transducer 250 is a linear element phased-array type wherein an angle 252 and focus of a plurality of ultrasonic beams 254 are variably selected by controlling the timing of the ultrasonic pulse and reception for each element of transducer 250. In an alternative embodiment, transducer 250 comprises at least one non-phased array transducer configured to transmit ultrasonic beams into a component at a plurality of steering angles. Using one or more transducers may permit ultrasonic viewing of portions of the component that may not be able to be viewed using a phased-array transducer. Components may be tested separately from other pieces of an assembly as well as part of the assembly. In addition, components with portions that are inaccessible to known testing methods may be tested using one or more non-phased-array transducers and/or phased-array transducers.

Figure 4:
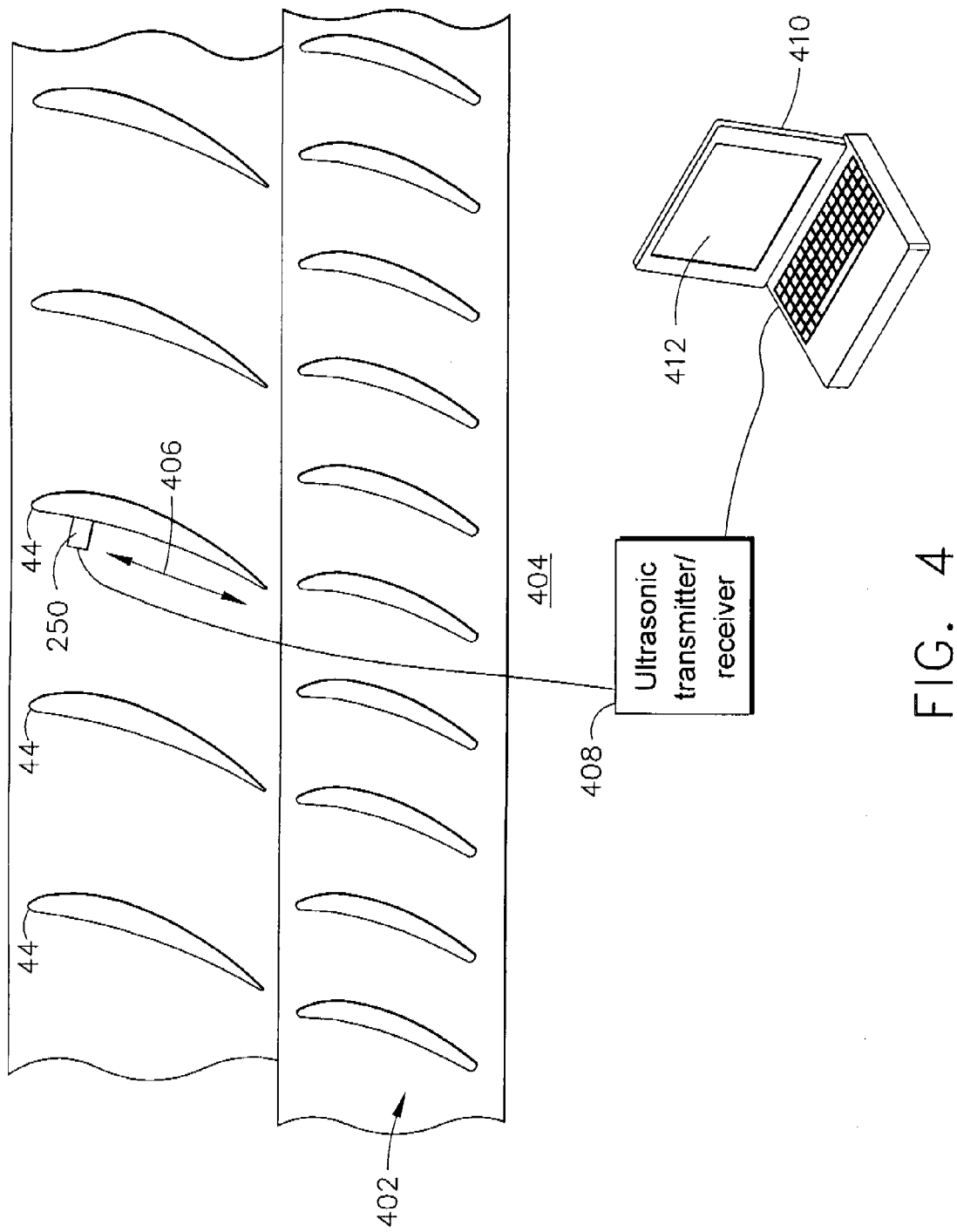
FIG. 4 is a radial perspective view of a row of inlet guide vanes and a row of compressor blades that may be used with the gas turbine engine shown in FIG. 1.

FIG. 4 is a radial perspective view of a row of inlet guide vanes 402 and a row of blades 44 that may be used with gas turbine engine 10 (shown in FIG. 1). In one embodiment, transducer 250 is transitioned from an accessible area 404 upstream from inlet guide vanes 402, through inlet guide vanes 402. The inlet guide vanes 402 may be blocked in a full open position to facilitate testing of blades 44.

Transducer 250 is held in place against each blade 44 in turn, and is translated mechanically, or scanned automatically, in a substantially axial direction across blade pressure side 212. During the scanning, an ultrasonic beam from transducer 250 is electronically swept through a range of angles 252 by establishing precise delay times in the pulsing and receiving of the ultrasonic energy. As each blade 44 is scanned, an ultrasonic transmitter/receiver 408 generates ultrasonic pulses to excite transducer 250, and then receives echoes from blade 44 to facilitate detecting flaws, which may have developed within dovetail 206. Data received from each azimuthal position includes an axial position of the transducer 250 along blade 44, and a distance from the test surface on the face of blade 44 to each recorded reflector, which may include a structural edge of dovetail 206. The data is indicative of a structure of dovetail 206, and/or a flaw, and beam angle 252 at which each echo was detected. In the exemplary embodiment, the data is transmitted to a processor 410 such as, but not limited to a laptop computer, a personal digital assistant (PDA), a data collector, or a network connection. In an alternative embodiment, the echo data and transducer position data may be received by separate processors. In the exemplary embodiment, processor 410 includes a display 412 to monitor results of each scan and operation of the scan. As used herein, the term "processor" also refers to microprocessors, central processing units (CPU), application specific integrated circuits (ASIC), logic circuits, and any other circuit or processor capable of executing inspection system, as described herein.

Figure 5:
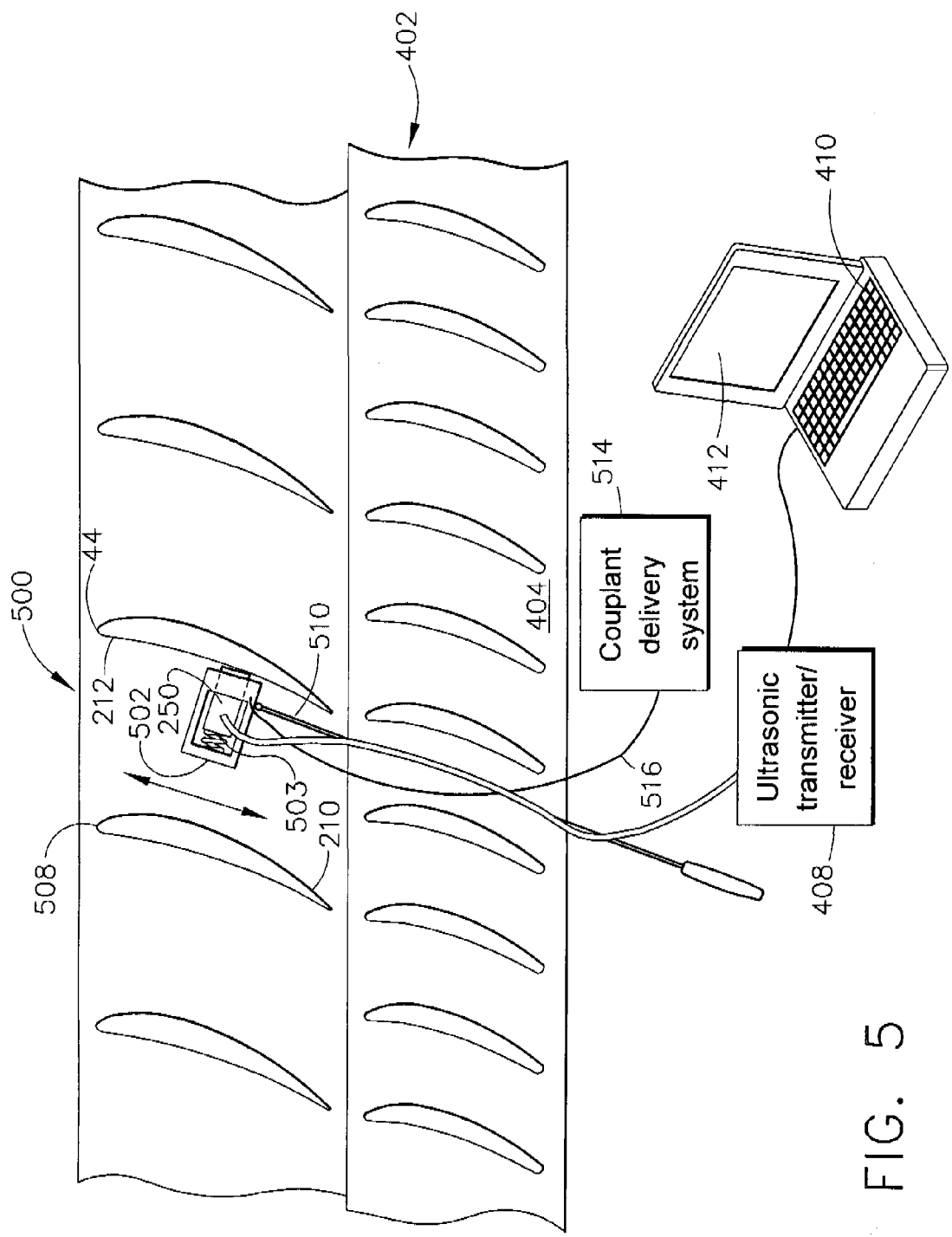
FIG. 5 is a perspective view of an exemplary manual scan embodiment of an ultrasonic testing system that may be used with the gas turbine engine shown in FIG. 1.

FIG. 5 is a perspective view of an exemplary ultrasonic testing system 500 that may be used with gas turbine engine 10 (shown in FIG. 1). Within system 500, transducer 250 is coupled to a guide housing 502 that includes a biasing mechanism 503 that facilitates maintaining a close coupling of transducer 20 to pressure side 212 of blade 44. Guide housing 502 coupled to a manipulator rod 510 that extends from guide housing 502, through inlet guide vanes 402 to accessible area 404. A couplant delivery system 514 that may include, for example, a pump and a reservoir provides a supply of acoustic couplant to transducer 250 through a tube 516 during scanning.

During operation, guide housing 502 is slidably coupled to blade 44 and provides support to transducer 250 and attached components during the scan. Manipulator rod 510 is extended through inlet guide vanes from accessible area 404, where an operator may operatively slide transducer 250 across blade 44 while operating couplant delivery system 514, transmitter/receiver 408, and processor 410. The axial position of transducer 250 with respect to blade 44 may be input by the user is response to prompts from processor 410. Processor 410 may include data acquisition and/or analysis software executing thereon that receives data from transmitter/receiver 408 that displays simultaneously the data recorded for all beam angles as a polar plot, creating a cross-sectional view called a "sector scan" image. The sector scan image may include the echoes received from dovetail 206 and cracks or flaws located therein. The positions of the reflectors may be measured directly from the sector scan image. If a crack or flaw is present on the opposite surface in dovetail 206, its image will be displayed among the reflectors on display 412 or sent directly over a network to an analysis location (not shown). The position, depth, and dimension of the crack or flaw may be measured directly from the image shown on display 412.

Figure 6:
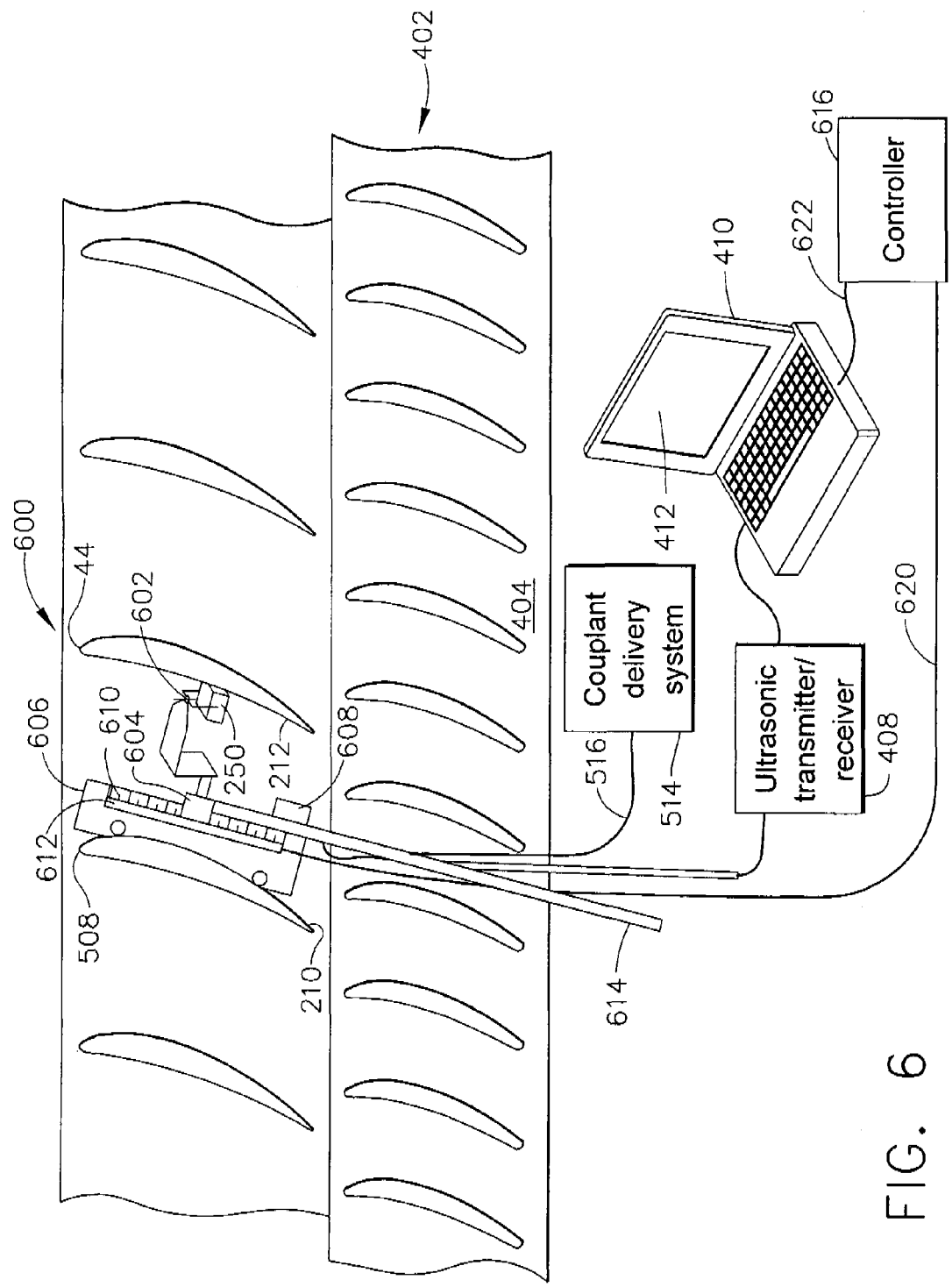
FIG. 6 is a perspective view of an exemplary automatic scan embodiment of the ultrasonic testing system shown in FIG. 5.

FIG. 6 is a perspective view of an exemplary automatic scan embodiment of ultrasonic testing system 600 that may be used with gas turbine engine 10 (shown in FIG. 1). In the exemplary embodiment, within system 600, transducer 250 is pivotally coupled to a gimbal 602, which is coupled to a carriage 604. Transducer 250 may be biased within carriage 604 to facilitate contact between transducer 250 and pressure side 212 of blade 44. Carriage 604 is slidably coupled to a support fixture 606, which is coupled to suction side 210 of adjacent support blade 508. An actuator 608 is coupled to support fixture 606 through a gear train 610. In the exemplary embodiment, actuator 608 is a stepper motor. In an alternative embodiment, actuator 608 is a linear actuator. Actuator 608 and gear train 610 cooperate to translate transducer 250 laterally across blade 44 during a scan. An encoder 612 generates a carriage position signal relative to a position of carriage 604 along blade 44. A positioning handle 614 is coupled to fixture 606 to facilitate guiding fixture 606 from accessible area 404 through inlet guide vanes 402 into position between blades 44 and 508.

Encoder 612 transmits transducer position data to processor 410 to automate the data collection process. Stepper motor controller 616 is communicatively coupled to stepper motor 608 through a conduit 620, which may be, but not limited to, a copper wire, fiber optic, or wireless link. Stepper motor controller 616 is also communicatively coupled to processor 410 through a conduit 622, which may be, but not limited to, a copper wire, fiber optic, or wireless link.

During operation, components of system 600 are positioned in an initial scan position. In the exemplary embodiment, processor 410 is activated to begin an automatic scan. In an alternative embodiment, the scan may be controlled manually by operator input to processor 410 and/or controller 616. Scan control software executing in processor 410 may control transmitter/receiver 408, and motor controller 604 to record sector scan images and transducer position along blade 44 during the scan. In an alternative embodiment, couplant delivery system 514 is controlled by the scan control software. At the end of scan, processor 410 stops taking data and prompts the user to reposition system 600 to scan the next blade. Scanning continues with each blade scanned in turn until all blades are scanned. Repositioning of rotor wheel 50 to maintain accessibility to blades 44 may be necessary.

Figure 7:
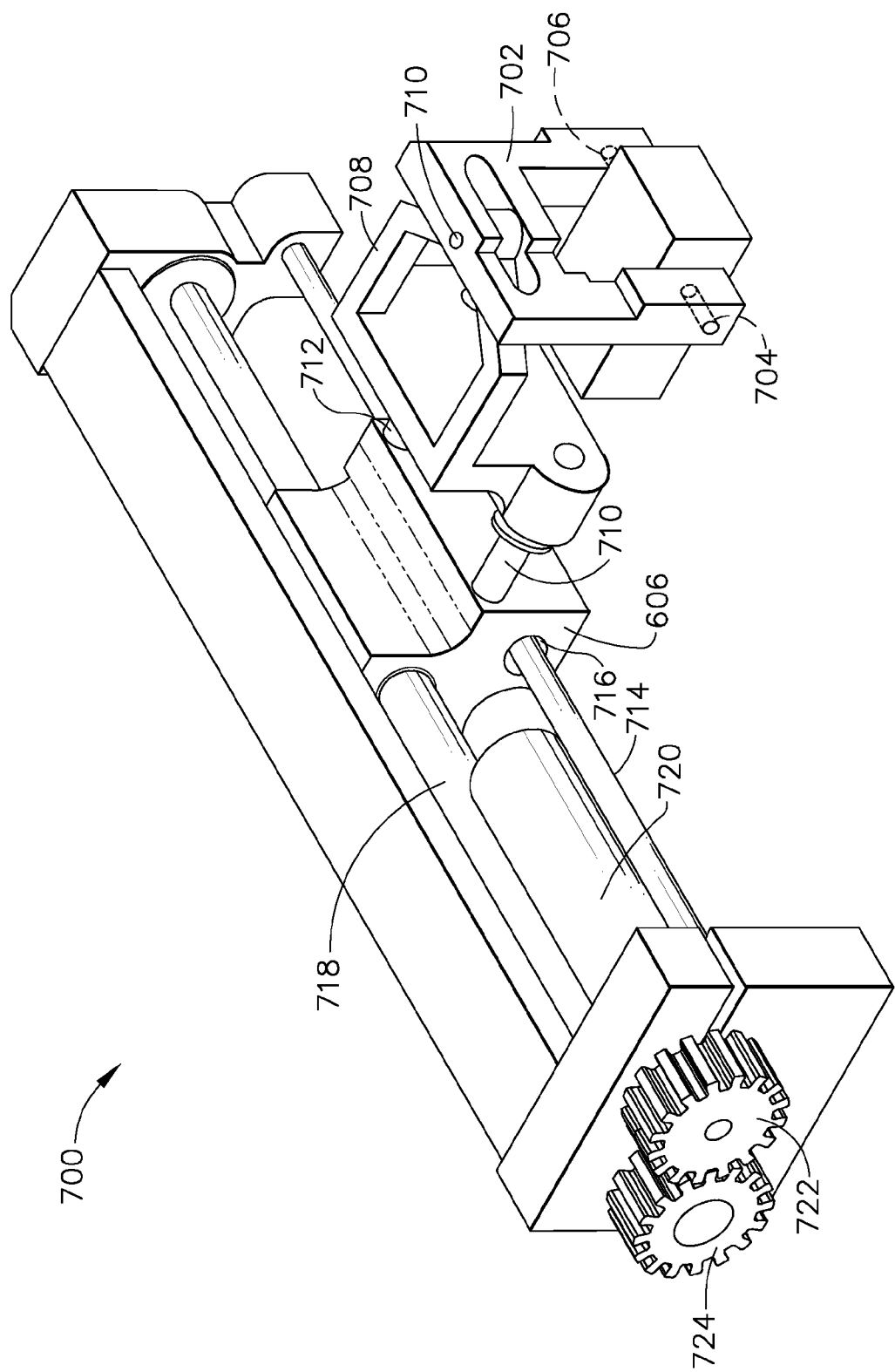
FIG. 7 is a detailed perspective view of an exemplary assembly 700 that may be used with the system shown in FIG. 6.

FIG. 7 is a detailed perspective view of an exemplary assembly 700 of transducer 250, gimbal 602, carriage 604 and support fixture 606 that may be used with system 600 (shown in FIG. 6). In the exemplary embodiment, assembly 700 includes transducer 250 pivotally coupled to a vertical gimbal 702 through a pin 704 and a pin 706. Vertical gimbal 702 is pivotally coupled to a slide gimbal 708 through a pin 710. Vertical gimbal 708 is slidably coupled to carriage 606 through a slide rod 710 and a slide rod 712. Carriage 606 is supported through a non-rotating rod 714, which passes through an aperture therethrough. A ball screw 718 engages carriage 606 to provide a lateral translational force to move carriage laterally along rod 714. A stepper motor 720 is rotatably coupled to ball screw 718 through a motor gear 722 and a complementary ball screw gear 724 to provide a rotational force to ball screw 718.

Figure 8:
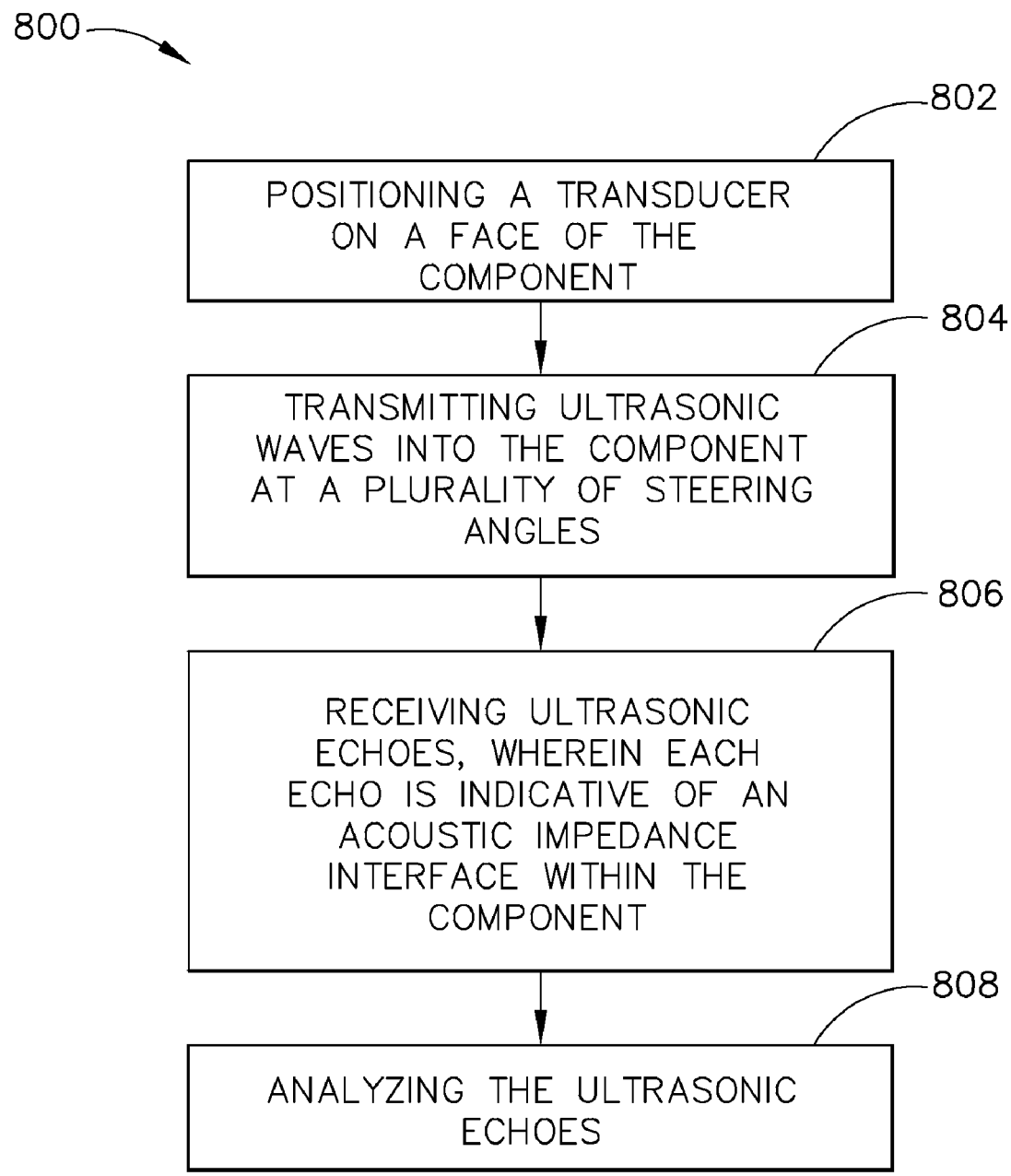
FIG. 8 is a block diagram of an exemplary method for ultrasonically testing a component of an assembly.

FIG. 8 is a block diagram of an exemplary method 800 for ultrasonically testing a component 44 of a rotatable member 50 of a rotary machine 10 while the rotatable member remains positioned within a casing (not shown) of an assembled rotary machine 10. In the exemplary embodiment, a linear element phased-array ultrasonic transducer is positioned 802 on a face of a turbine blade attached to a turbine rotor wheel. The transducer is positioned on each blade in turn during the testing procedure. Because the turbine remains assembled during the testing, the transducer is fed through the turbine inlet guide vanes, which may be blocked fully open. The transducer is positioned at the base of the blade airfoil radially outward from the blade platform and slid axially along a predetermined scan path while in contact with the blade. During the scan, the transducer transmits 804 ultrasonic waves into an inaccessible portion of the blade such that the phased-array technique steers the waves at a plurality of angles from an angle normal to the face of the blade to an angle wherein the blade dovetail may be interrogated by the ultrasonic waves. The transducer receives 806 ultrasonic echoes as a result of the ultrasonic waves impinging on an acoustic impedance interface within the blade dovetail and being reflected. The transducer receives at least some of the ultrasonic energy that is reflected back into the transducers' field of view. The echoes may be indicative of dovetail structures and flaws, such as cracks, that may have developed within the dovetail. The echoes are transmitted to a processor for analyzing 808 the ultrasonic echoes to determine the crack location and dimensions. The result may be displayed on a local display or may be transmitted to a remote location for further analysis.

The above-described ultrasonic testing method and apparatus is cost-effective and highly reliable for testing blades that remain installed on a turbine rotor in an assembled machine. Specifically, the dovetail area of the turbine blades is inaccessible to visual, eddy current, dye penetrant, and other test methods when the turbine is assembled. The method permits an inspection of blades without the heretofore attendant disassembly of the turbine and removal of the turbine blades to permit early detection of fatigue cracking in the primary location from which the cracks originate. By inspecting without removal of the blades, the inspection is less disruptive to the commercial operation of the machines and can be easily scheduled and accomplished within scheduled downtimes. As a result, the methods and apparatus described herein facilitate ultrasonic testing in a cost-effective and reliable manner.

Exemplary embodiments of ultrasonic testing systems are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A method of non-destructive evaluation (NDE) testing a component coupled to a rotatable member of a rotary machine while the rotatable member remains coupled within an assembled rotary machine, said method comprising:
   positioning a transducer on a face of the component along a substantially axial path of an axis of rotation of the rotatable member using an actuator;
   transmitting ultrasonic waves into a root of the component;
   receiving ultrasonic echoes, wherein each received echo is indicative of an acoustic impedance interface within the component; and
   analyzing the ultrasonic echoes.

2. A method in accordance with claim 1 wherein transmitting ultrasonic waves comprises transmitting ultrasonic waves at a plurality of steering angles using a phased array transducer.

3. A method in accordance with claim 1 wherein the rotatable member includes a plurality of slots, each component includes an attachment portion that is engaged in at least one of the slots, said transmitting ultrasonic waves comprises directing the waves into an attachment portion of the component.

4. A method in accordance with claim 1 wherein the rotatable member includes a plurality of slots, each component includes an attachment portion that is engaged in at least one of the slots, said method further comprises determining a flaw position and dimension from the echoes.

5. A method in accordance with claim 1 further comprising delivering fluid to the transducer to form a layer of fluid for coupling energy between the transducer and the component.

6. A method in accordance with claim 1 wherein positioning a transducer on a face of the component along a substantially axial path of an axis of rotation of the rotatable member further comprises automatically repositioning the transducer on the component face along the substantially axial path of the axis of rotation of the rotatable member using an actuator.

7. A method in accordance with claim 1 wherein analyzing comprises:
   receiving transducer position information from a transducer position encoder; and
   correlating a transducer position with echo data to determine a flaw location.

8. A method for ultrasonically testing a turbine blade coupled on a turbine rotor while the rotor remains positioned within an assembled turbine, said method comprising:
   scanning along the face of the turbine blade in a substantially axial direction of an axis of rotation of the turbine rotor using a phased-array ultrasonic transducer;
   transmitting ultrasonic waves from the blade root into a dovetail of the blade at a plurality of steering angles;
   receiving ultrasonic echoes from the dovetail wherein the echoes are indicative of dovetail structure features and dovetail flaws; and
   analyzing the ultrasonic echoes to determine a location and dimension of the features and flaws.

9. An ultrasonic testing system for testing a component of a rotatable member of a rotary machine while the rotatable member remains coupled within an assembled rotary machine, said system comprising:
   a transducer configured to transmit ultrasound waves into and receive ultrasound echoes from the component;
   a positioning fixture coupled to said transducer, such that said positioning fixture is supported from the component and configured to position said transducer across a face of the component axially along an axis of rotation of the rotatable member while the transducer is transmitting and receiving ultrasonic echoes;
   a transmitter/receiver for transmitting signals to said transducer and for receiving signals from said transducer that are indicative of ultrasonic echoes from said transducer, wherein each echo is indicative of an acoustic impedance interface within the component;
   a processor for at least one of controlling outputs from said transmitter/receiver and receiving inputs from said transmitter/receiver; and
   a display for outputting information based on said ultrasonic echo data.

10. An ultrasound system in accordance with claim 9 wherein said transducer is a phased-array transducer that is configured to transmit ultrasonic waves at a plurality of steering angles.

11. An ultrasound system in accordance with claim 9, said positioning fixture configured to position said transducer, on the face of the component to facilitate ultrasonic waves being directed into an attachment portion of the component.

12. An ultrasound system in accordance with claim 9 wherein said positioning fixture comprises a biasing member to facilitate maintaining contact between said transducer and the component.

13. An ultrasound system in accordance with claim 9 wherein said positioning fixture comprises a body including a support coupling comprising at least one of a permanent magnet, a clamp, and a band.

14. An ultrasound system in accordance with claim 9 wherein said positioning fixture comprises a manual manipulator configured to reposition said transducer axially across the face of the component during a manual scan of the attachment portion.

15. An ultrasound system in accordance with claim 9 wherein said positioning fixture comprises a manipulator actuator configured to reposition said transducer axially along the face of the component during a scan of the attachment portion.

16. An ultrasound system in accordance with claim 9 wherein said positioning fixture comprises a manipulator actuator configured to automatically reposition said transducer axially across the face of the component during a scan of the attachment portion.

17. An ultrasound system in accordance with claim 9 further comprising a system for delivering fluid to said transducer such that a layer of fluid formed between said transducer and the component, said system configured to be controlled at least one of manually and automatically though said processor.

18. An ultrasound system in accordance with claim 17 wherein said system for delivering fluid includes:
   a coupling fluid supply source;
   a flexible hose extending between said coupling fluid supply source and said transducer; and
   a pump for transferring coupling fluid from said coupling fluid supply source through said flexible hose to said transducer.

19. An ultrasonic testing system for testing a turbine blade coupled to a turbine rotor with a blade dovetail, while the rotor remains positioned within an assembled turbine, said system comprising:
   an array transducer configured to transmit and receive ultrasound waves into and from a face of the blade;
   a positioning fixture configured to position said transducer axially along an axis of rotation of the turbine rotor and across a face of the blade while the transducer is transmitting and receiving ultrasonic echoes, said positioning fixture comprising a transducer position encoder;
   a transmitter/receiver for transmitting signals to said transducer in a phased relationship such that the waves from said transducer are steered at a plurality of predetermined angles into the blade dovetail and for receiving signals from said transducer indicative of ultrasonic echoes from the blade dovetail;
   a display for outputting information based on the ultrasonic echoes; and
   a processor programmed to:
      control an output of said transmitter/receiver;

receive ultrasonic echo data from said transmitter/receiver;

receive transducer position information from said encoder; and determine a flaw location and dimension from the echo data and position information.

* * * * *